United States Patent [19]
Bacon et al.

[11] Patent Number: 5,670,136
[45] Date of Patent: Sep. 23, 1997

[54] 2,4,6-TRIIODO-5-SUBSTITUTED-AMINO-ISOPHTHALATE ESTERS USEFUL AS X-RAY CONTRAST AGENTS FOR MEDICAL DIAGNOSTICS IMAGING

[75] Inventors: Edward R. Bacon, Audubon, Pa.; Sol J. Daum, Albany, N.Y.; Kimberly G. Estep, Pottstown, Pa.

[73] Assignee: NanoSystems L.L.C., Collegeville, Pa.

[21] Appl. No.: 586,363

[22] Filed: Jan. 16, 1996

Related U.S. Application Data

[63] Continuation of Ser. No. 265,590, Jun. 24, 1994, abandoned.
[51] Int. Cl.$^6$ .................................................. A61K 49/04
[52] U.S. Cl. .................... 424/9.455; 424/9.45; 560/47
[58] Field of Search .......................... 424/9.45, 9.455; 560/47

[56] References Cited

U.S. PATENT DOCUMENTS

| | | | |
|---|---|---|---|
| 2,820,814 | 1/1958 | Ginsberg | 424/9.455 |
| 3,097,228 | 7/1963 | Larsen | 560/47 |
| 3,144,479 | 8/1964 | Odendorf | 560/47 |
| 4,364,921 | 12/1982 | Speck et al. | 564/153 |
| 5,344,638 | 9/1994 | Illig et al. | 424/9.45 |

FOREIGN PATENT DOCUMENTS

| | | |
|---|---|---|
| 241516 | 2/1960 | Australia . |
| 498482 | 8/1992 | European Pat. Off. . |
| 866184 | 4/1961 | United Kingdom . |

OTHER PUBLICATIONS

Obendorf (Chem. Ab. 57:4603i) (1963).
Siggins et al (J. Chem. Med. 8(5) 728–30 (1965).

*Primary Examiner*—Brian M. Burn
*Attorney, Agent, or Firm*—Rudman & Associates

[57] ABSTRACT

Compounds having the structure:

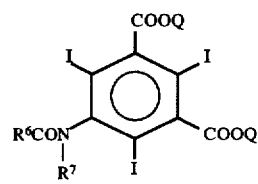

wherein Q is

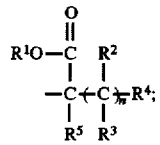

n is an integer from 0 to 20;

$R^1$ is H, alkyl, fluoroalkyl, cycloalkyl, aryl, aralkyl, alkoxyalkyl or acetamidoalkyl;

$R^2$, $R^3$, $R^4$ and $R^5$ are independently H, alkyl, fluoroalkyl, halogen, hydroxy, acylamino, acetamidoalkyl, cyano, sulfonyl, carboxamido or sulfonamido;

$R^6$ is alkyl, cycloalkyl, aryl, or aralkyl; and $R^7$ is H or —$COR^6$ are useful as contrast agents in medical diagnostic x-ray imaging compositions and methods.

7 Claims, No Drawings

2,4,6-TRIIODO-5-SUBSTITUTED-AMINO-ISOPHTHALATE ESTERS USEFUL AS X-RAY CONTRAST AGENTS FOR MEDICAL DIAGNOSTICS IMAGING

This is a Continuation of application Ser. No. 08/265,590; filed 24 Jun. 1994, (now abandoned).

FIELD OF INVENTION

This invention relates to iodinated aroyloxy esters which find particular utility as x-ray contrast agents in medical diagnostic imaging.

BACKGROUND OF THE INVENTION

X-ray imaging is a well known and extremely valuable tool for the early detection and diagnosis of various disease states in the human body. The use of contrast agents for image enhancement in medical x-ray imaging procedures is widespread. An excellent background on iodinated and other contrast agents for medical imaging is provided by D. P. Swanson et al, *Pharmaceuticals in Medical Imaging*, 1990, MacMillan Publishing Company.

U.S. Pat. No. 3,097,228 describes derivatives of 2,4,6-triiodobenzoyloxyalkanoic acids having the structure

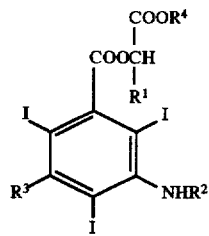

wherein $R^1$ is H or lower alkyl; $R^2$ is H or lower alkanoyl; $R^3$ is H or lower alkanoylamino and $R^4$ is lower alkyl. The agents are useful as x-ray contrast agents for visualizing the gall bladder (cholecystography) when administered orally, in the free acid form or in the form of a non-toxic salt, or intravenously, in the form of water soluble, non-toxic salt.

Bacon et al, commonly assigned U.S. patent application Ser. No. 07/990,987 filed December 16, 1992 (now U.S. Pat. No. 5,322,679) describes iodinated aroyloxy esters which are useful as contrast agents in x-ray imaging compositions and methods. However, all of the compounds described by Bacon et al feature an ester group linked through a $C_2$ or higher alkylene group to another ester group on an iodinated aromatic ring.

U.S. Pat. No. 4,364,921 describes triiodinated isophthalic acid diamides as nonionic x-ray contrast media. All of the described compounds contain amide residues in the 3- and 5- positions of the 2,4,6-triiodoisophthalic acid.

EP-A 498,482 describes nanoparticulate x-ray contrast compositions which have proven to be extremely useful in medical imaging. The compositions comprise particles of an organic x-ray contrast agent and a surface modifier adsorbed on the surface thereof and have an effective average particle size of less than 400 nm. The agents can be delivered to a specific tissue or fluid site, e.g., the blood pool, liver, spleen, kidney or lymph nodes. EP-A 498,482 describes derivatives of diatrizoate, iothalamate, metrizoate and iodipamide containing an

wherein R' is alkyl. However, EP-A 498,482 does not suggest the 2,4,6-triiodo-5-substituted-isophthalate esters of this invention.

Moreover, it has been, discovered that some of the derivatives described in EP-A 498,482 can exhibit multiple crystal forms, i.e., polymorphs, e.g., when recrystallized from various solvents. The reasons for this behavior are not completely understood, but, in any event, multiple crystal forms are disadvantageous for a variety of reasons. For example, the presence of multiple crystal forms renders scale-up problematic due to the lack of reproducibility of the results obtained, including, e.g., in chemical manufacturing and in the milling process. Furthermore, particulate contrast agents in certain in vivo applications can exhibit less than fully satisfactory solubility profiles and/or enzymatic stability, e.g., in plasma and blood.

Consequently, it would be highly desirable to provide poorly soluble x-ray contrast agents which exhibit a consistent and reproducible crystal morphology, and improved solubility profiles and enzymatic stability.

SUMMARY OF THE INVENTION

We have discovered and synthesized certain novel esters of 2,4,6-triiodo-5-substituted-amino-isophthalic acid which exhibit a consistent and reproducible crystal morphology, and improved solubility profiles and enzymatic stability.

More specifically, in accordance with this invention, there are provided 2,4,6-triiodo-5-substituted-amino-isophthalic esters and acids having the structure I:

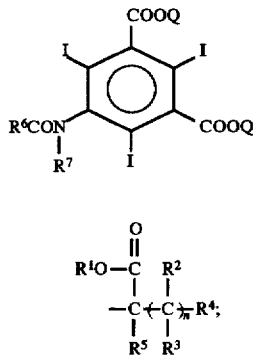

wherein Q is n is an integer from 0 to 20;

$R^1$ is H, alkyl, fluoroalkyl, cycloalkyl, aryl, aralkyl, alkoxyalkyl or acetamidoalkyl;

$R^2$, $R^3$, $R^4$ and $R^5$ are independently H, alkyl, fluoroalkyl, halogen, hydroxy, acylamino, acetamidoalkyl, cyano, sulfonyl, carboxamido or sulfonamido;

$R^6$ is alkyl, cycloalkyl, aryl, or aralkyl; and $R^7$ is H or —$COR^6$.

It is an advantageous feature of this invention that novel iodinated aroyloxy esters and acids are provided which find particular utility in x-ray contrast compositions.

It is another advantageous feature of this invention that compounds are provided having improved solubility profiles and enzymatic stability.

Still another advantageous feature of this invention is that compounds are provided which exhibit a consistent crystal morphology during purification and thus are particularly amenable to reproducible scale-up.

DESCRIPTION OF PREFERRED EMBODIMENTS

In structure I above, each Q independently represents a

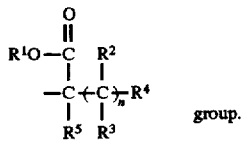
group.

n represents an integer from 0–20 inclusive. In preferred embodiments, n is 0, 1, 2, 3 or 4.

$R^1$ represents H; linear or branched alkyl, preferably containing from 1 to 20, more preferably from 1 to 14, and most preferably from 1 to 8 carbon atoms such as methyl, ethyl, propyl, isopropyl, butyl, pentyl, hexyl and the like; fluoroalkyl, the alkyl portion of which is as defined above and containing from 1 to (2m+1) fluorine atoms (where m=the number of carbon atoms in the alkyl group), such as trifluoromethyl; cycloalkyl, preferably containing from 3 to 8 carbon atoms such as cyclopropyl, cyclobutyl, cyclopentyl and cyclohexyl; aryl, preferably containing from 6 to 10 carbon atoms, such as phenyl and naphthyl; aralkyl, preferably containing from 7 to 12 carbon atoms, such as benzyl; alkoxyalkyl, the alkyl portions of which preferably contain from 1 to 20 carbon atoms as defined for alkyl above; or acetamidoalkyl, i.e.,

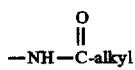

wherein alkyl is as defined above.

$R^2, R^3, R^4$ and $R^5$ are independently H; linear or branched alkyl, preferably containing from 1 to 20, more preferably 1 to 8 carbon atoms such as methyl, ethyl, propyl, isopropyl, butyl, pentyl, hexyl and the like; fluoroalkyl, the alkyl portion of which is as described above and containing from 1 to (2m+1) fluorine atoms (where m=the number of carbon atoms in the alkyl group), such as trifluoromethyl; halogen, such as fluorine, chlorine, bromine or iodine; hydroxy; acylamino, i.e., a

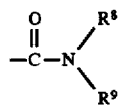

group; acetamidoalkyl, i.e.,

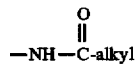

wherein alkyl is as defined above; cyano; sulfonyl; carboxamido; sulfonamido and the like. However, reactive substituents such as halogen, hydroxy, and acylamino are not preferred on the carbon atoms closest to the ester groups. Thus, in particularly preferred embodiments, $R^5$ is H, alkyl, fluoroalkyl, acetamidoalkyl, cyano, sulfonyl, carboxamido or sulfonamido. The reason for this is that when $R^5$ is halogen, hydroxy or acylamino, the compounds tend to be more reactive and less useful as particulate x-ray contrast agents.

$R^6$ represents alkyl, as defined above; cycloalkyl, preferably containing from 3 to 8 carbon atoms such as cyclopropyl, cyclobutyl, cyclopentyl and cyclohexyl; aryl, preferably containing from 6 to 10 carbon atoms such as phenyl or naphthyl; or aralkyl, preferably containing from 7 to 12 carbon atoms, such as benzyl.

$R^7$ represents H or —$COR^6$, wherein $R^6$ is as defined above.

$R^8$ and $R^9$ are independently a substituent as defined for $R^2$–$R^5$ above, or $R^8$ and $R^9$, taken together with the nitrogen atom to which they are attached, represent a 4–7 membered saturated or unsaturated nitrogen containing ring such as piperidyl, piperizinyl, pyrrolidinyl, and the like.

The following are specific illustrative examples of preferred compounds of this invention that have been prepared:

Bis-[1-(ethoxycarbonyl)propyl]2,4,6-triiodo-5-acetylamino-isophthalate;
Bis-[1-(ethoxycarbonyl)pentyl]2,4,6-triiodo-5-acetylamino-isophthalate;
Bis-[1-(ethoxycarbonyl)ethyl]2,4,6-triiodo-5-acetylamino-isophthalate;
Bis-[1-(ethoxycarbonyl)butyl]2,4,6-triiodo-5-acetylamino-isophthalate;
Bis-[1-(ethoxycarbonyl)methyl]2,4,6-triiodo-5-acetylamino-isophthalate.

Preferred compounds of this invention conform to structure I above, as indicated in the Table set forth below:

| Compound | $R^1$ | n | $R^2$ | $R^3$ | $R^4$ | $R^5$ | $R^6$ | $R^7$ |
|---|---|---|---|---|---|---|---|---|
| 1 | —$C_2H_5$ | 2 | H | H | H | H | —$CH_3$ | H |
| 2 | —$C_2H_5$ | 1 | H | H | H | H | —$CH_3$ | H |
| 3 | —$C_2H_5$ | 4 | H | H | H | H | —$CH_3$ | H |
| 4 | —$C_2H_5$ | 3 | H | H | H | H | —$CH_3$ | H |
| 5 | —$C_2H_5$ | 0 | — | — | H | H | —$CH_3$ | H |

The compounds of this invention can be prepared by contacting the carboxylate of 2,4,6-triiodo-5-substituted-amino-isophthalic acid with a functionalized ester having the formula

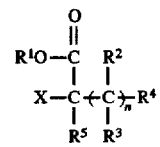

wherein X is a leaving group and n and $R^1$–$R^5$ are as defined above, in a suitable solvent. Suitable leaving groups include halogen, such as Br, I and Cl, and sulfonyloxy, such as methanesulfonyloxy and toluenesulfonyloxy. The carboxylates of iodinated aromatic acids and functionalized esters useful as the starting materials in the preparation of the compounds of this invention are known compounds and/or can be prepared by techniques known in the art. For example, suitable esters include commercially available bromoester and chloroester derivatives as exemplified below. A general reaction scheme is as follows:

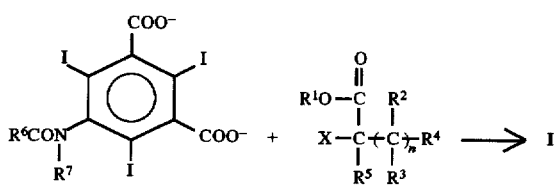

The reaction can take place at various temperatures ranging between −78° C. and 100° C., and preferably between −40° C. and 50° C. For convenience, the reaction can take place at ambient pressure, however, higher and lower pressures are contemplated.

The reaction can take place in any suitable solvent. Suitable solvents include N,N-dimethylformamide (DMF) and dimethylsulfoxide (DMSO).

The iodinated compounds can contain substituents which do not deleteriously affect the contrast enhancing capability of the compound. For example, the alkyl, cycloalkyl, aryl, aralkyl and alkoxy groups in structure I above can be unsubstituted or substituted with various substituents which do not adversely affect the stability or efficacy of the compounds as x-ray contrast agents such as alkyl, cycloalkyl, aryl, aralkyl, alkoxy, hydroxy, acyloxy, halogen, such as chlorine, bromine and iodine, acylamino, carboalkoxy, carbamyl and the like.

When used as an x-ray contrast agent, the compound of this invention preferably comprises at least about 35%, more preferably at least 40% iodine by weight.

In preferred embodiments, the compounds of this invention can be formulated into particulate x-ray contrast compositions, preferably nanoparticulate x-ray contrast compositions, as described in commonly-owned EP-A 498, 482. Preferred compounds exhibit a melting point of greater than 150° C. Such nanoparticulate compositions can be prepared by dispersing the compounds of the invention in a liquid dispersion medium, and wet grinding the compound in the presence of rigid grinding media and a surface modifier to form the nanoparticles. Alternatively, the surface modifier can be contacted with the compound after attrition. Preferred surface modifiers include nonionic surfactants.

In preferred embodiments, the surface modifier is a high molecular weight nonionic surfactant. Preferred surfactants include poloxamers such as Pluronic™ F68 and F108, which are block copolymers of ethylene oxide and propylene oxide, poloxamines, such as Tetronic™ 908 (also known as Poloxamine 908), which is a tetrafunctional block copolymer derived from sequential addition of propylene oxide and ethylene oxide to ethylenediamine, and dialkyl esters of sodium sulfosuccinic acid, such as dioctylsulfosuccinate sodium (DOSS). The concentrations of the surface modifier can vary from about 0.1–75%, preferably 1–60%, and more preferably 10–30% by weight based on the total combined weight of the contrast agent and surface modifier.

In preferred embodiments, the x-ray contrast composition in the form of surface modified nanoparticles can be associated with a cloud point modifier to further enhance stability during steam heat autoclaving, i.e., the cloud point modifier can reduce particle aggregation during heat sterilization. Preferred cloud point modifiers include nonionic cloud point modifiers, such as polyethylene glycols such as PEG 400, propylene glycol, ethanol, hydroxypropylcyclodextrin and glycerol; ionic cloud point modifiers, such as those described in U.S. Pat. No. 5,298,262 including dialkylesters of sodium sulfosuccinic acid such as the dioctylester of sodium sulfosuccinic acid (DOSS); and charged phospholipids, such as diacylphosphatidyl glycerol and dimyristoylphosphatidyl glycerol. The cloud point modifier can be present in an amount of 0.005–50%, preferably 0.01–30% and more preferably 0.05–20% by weight based on the total weight of the x-ray contrast composition.

The x-ray contrast compositions of this invention comprise the above-described compounds, preferably in the form of particles, and a physiologically acceptable carrier therefor. For example, the particles can be dispersed in an aqueous liquid which serves as the carrier for the x-ray contrast agent. Other suitable carriers include liquid carriers such as mixed aqueous and nonaqueous solvents, such as alcohol; gels; gases, such as air; and powders.

The x-ray contrast composition can comprise from about 1–99.9, preferably 2–45 and more preferably 10–25% by weight of the above-described particles, the remainder of the composition being the carrier, additives and the like. Compositions up to about 100% by weight of the particles are contemplated when the composition is in a lyophilized form.

The dose of the contrast agent to be administered can be selected according to techniques known to those skilled in the art such that a sufficient contrast enhancing effect is obtained. Typical doses can range from 20 to 350 mg of iodine per kilogram of body weight of the subject for many imaging applications. For some applications, e.g., lymphography, lower doses, e.g., 0.5–20 mg I/kg, can be effective. For blood pool imaging, the dose can range from 50 to 350 mg of iodine per kilogram of body weight and preferably from 100 to 250 mg of iodine per kilogram of body weight.

The x-ray contrast composition can contain one or more conventional additives used to control and/or enhance the properties of the x-ray contrast agent. For example, thickening agents such as dextran or human serum albumin, buffers, viscosity regulating agents, suspending agents, peptizing agents, anti-clotting agents, mixing agents, and other drugs and the like can be added. A partial listing of certain specific additives includes gums, sugars such as dextran, human serum albumin, gelatin, sodium alginate, agar, dextrin, pectin and sodium carboxymethyl cellulose. Such additives, surface active agents, preservatives and the like can be incorporated into the compositions of the invention.

A method for diagnostic imaging for use in medical procedures in accordance with this invention comprises administering to the body of a test subject in need of an x-ray an effective contrast producing amount of the above-described x-ray contrast composition. In addition to human patients, the test subject can include mammalian species such as rabbits, dogs, cats, monkeys, sheep, pigs, horses, bovine animals and the like. Thereafter, at least a portion of the body containing the administered contrast agent is exposed to x-rays to produce an x-ray image pattern corresponding to the presence of the contrast agent. The image pattern can then be visualized. For example, any x-ray visualization technique, preferably, a high contrast technique such as computed tomography, can be applied in a conventional manner. Alternatively, the image pattern can be observed directly on an x-ray sensitive phosphor screen-silver halide photographic film combination.

The compositions of this invention can be administered by a variety of routes depending on the type of procedure and the anatomical orientation of this tissue being examined. Suitable administration routes include intravascular (arterial or venous) administration by catheter, intravenous injection, rectal administration, subcutaneous administration, intramuscular administration, intralesional administration, intrathecal administration, intracisternal administration, oral administration, administration via inhalation, administration directly into a body cavity, e.g., arthrography, and the like.

In addition to preferred applications, i.e., for blood pool and lymph node imaging, the x-ray contrast compositions of this invention are also expected to be useful as contrast agents for any organ or body cavity. For example, the compositions of this invention are expected to be useful as angiographic contrast media, urographic contrast media, myelographic contrast media, gastrointestinal contrast media, cholecystographic and cholangiographic contrast media, arthrographic contrast media, hysterosalpingographic contrast media, oral contrast media and bronchographic contrast media.

The following examples further illustrate the invention.

EXAMPLE 1 preparation of Bis-[1-(ethoxycarbonyl) propyl]2,4,6-triiodo-5-acetylamino-isophthalate Sodium metal (1.9 g, 82.6 mmole) was dissolved in 500 ml of absolute ethanol followed by the addition of 25 g (42 mmole) of 5-substituted-2,4,6-triiodoisophthalic acid. After stirring for 30 minutes the solvent was removed under vacuum to give 36.1 g of the di-sodium salt which was dried under high vacuum and used without further purification.

To a suspension of the sodium salt (10 g, 15.5 mmole) described above in 50 ml of DMF was added ethyl 2-bromobutyrate and the mixture was stirred at ambient temperature for 6 hrs at which point solution was observed. After heating for 1 hr on a steam bath, the solution was cooled and added to a mixture of ice and water. The desired product crystallized from the aqueous solution overnight and was collected by filtration and dried under vacuum to give an essentially quantitative yield of white solid, mp 195°–205° C.; CI-MS: MH$^+$830. The $^1$H-NMR (300 MHz) spectral data was consistent with the desired material.

Calculated for $C_{22}H_{26}I_3NO_9$: C 31.87, H 3.16, I 45.92, N 1.69; Found: C 31.81, H 3.17, I 45.94; N 1.64.

EXAMPLE 2

Preparation of Bis-[1-(ethoxycarbonyl)pentyl]2,4,6-triiodo-5-acetylamino-isophthalate To a mixture of 5-acetylamino-2,4,6-triiodoisophthalic acid (80 g, 133.1 mmole) and sodium carbonate (28 g, 266.7 mmole) in dry DMF (300 ml) was added ethyl 2-bromohexanoate (40.1 ml, 266.7 mmole). After stirring at ambient temperature overnight, the bulk of the solvent was removed under vacuum and the concentrated residue was poured into 4 l of water. The precipitated solid was collected and recrystallized from DMF/water to give 98.5 g of product, mp 118°–120° C. after drying at 90° C. under high vacuum. The $^1$H-NMR (300 MHz) spectral data was consistent with the desired material.

Calculated for $C_{26}H_{34}I_3NO_8$: C 35.24, H 3.84, I 43.00, N 1.58; Found: C 35.35, H 3.66, I 43.01, N 1.49.

EXAMPLE 3

Preparation of Bis-[1-(ethoxycarbonyl)ethyl]2,4,6-triiodo-5-acetylamino-isophthalate In a manner similar to the procedures described in Examples 1 and 2 above, analytically pure compound, mp 160°–165° C., was prepared. The MS and 300 MHz-NMR spectral data were consistent with the desired product.

Calculated for $C_{20}H_{22}I_3NO_4$: C 29.99, H 2.77, N 1.75, I 47.52; Found: C 30.11, H 2.65, N 1.72, I 47.40.

EXAMPLE 4

Preparation of Bis-[1-(ethoxycarbonyl)butyl]2,4,6-triiodo-5-acetylamino-isophthalate In a manner similar to the procedures described in Examples 1 and 2 above, analytically pure compound, mp 155°–156° C., was prepared. The MS and 300 MHz-NMR spectral data were consistent with the desired material.

Calculated for $C_{24}H_{30}I_3NO_4$: C $_{33.63}$, H 3.53, N 1.63, I 44.41; Found: C 33.72, H 3.39, N 1.59, I 44.13.

EXAMPLE 5

Preparation of Bis-[1-(ethoxycarbonyl)methyl]2,4,6-triiodo-5-acetylamino-isophthalate In a manner similar to the procedures described in Examples 1 and 2 above, analytically pure compound, mp 194°–195° C., was prepared. The MS and 300 MHz-NMR spectral data were consistent with the desired material.

Calculated for $C_{18}H_{18}I_3NO_9$: C 27.97, H 2.35, I 49.25, N 1.87; Found: C 28.06, H 2.25, I 49.37, N 1.78.

The acids of the above-described esters can be prepared by any conventional technique known in the art. The acids and salts thereof are particularly useful as wetting agents and/or as surface modifiers in x-ray contrast compositions, particularly nanoparticulate x-ray contrast compositions.

The invention has been described in detail with particular reference to certain preferred embodiments thereof, but it will be understood that variations and modifications can be effected within the spirit and scope of the invention.

We claim:

1. A method of imaging a mammal's blood pool and lymph nodes, the method comprising (a) administering to the mammal a contrast enhancing effective amount of the x-ray contrast composition, the composition comprised of 1–99.9% by weight of nanoparticles of a compound having the structure

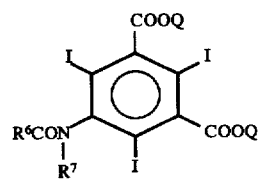

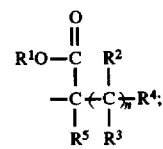

wherein Q is
n is an integer from 0 to 4;
$R^1$ is alkyl;
$R^2$, $R^3$, $R^4$ and $R^5$ are independently H or alkyl;
$R^6$ is alkyl; and
$R^7$ is H; and b) imaging the mammal's blood pool and lymph nodes.
2. The method of claim 1, wherein $R^5$ is H.
3. The method of claim 1, wherein $R^2$, $R^3$ and $R^4$ are H.
4. The method of claim 1, wherein $R^1$ is —$C_2H_5$.
5. The method of claim 1, wherein $R^1$ is —$C_2H_5$ and $R^2$, $R^3$, $R^4$ and $R^5$ are H.

6. The method of claim 1, wherein the compound is selected from the group consisting of:

Bis-[1-(ethoxycarbonyl)propyl]2,4,6-triiodo-5-acetylamino-isophthalate;

Bis-[1-(ethoxycarbonyl)pentyl]2,4,6-triiodo-5-acetylamino-isophthalate;

Bis-[1-(ethoxycarbonyl)ethyl]2,4,6-triiodo-5-acetylamino-isophthalate;

Bis-[1-(ethoxycarbonyl)butyl]2,4,6-triiodo-5-acetylamino-isophthalate;

Bis-[1-(ethoxycarbonyl)methyl]2,4,6-triiodo-5-acetylamino-isophthalate.

7. The method of claim 1 wherein the x-ray contrast composition further includes a pharmaceutically acceptable carrier.

* * * * *